United States Patent
Shroff et al.

(10) Patent No.: US 10,506,806 B2
(45) Date of Patent: Dec. 17, 2019

(54) AGROCHEMICAL FORMULATIONS

(71) Applicant: UPL Limited, Mumbai (IN)

(72) Inventors: Jaidev Rajnikant Shroff, Mumbai (IN); Vikram Rajnikant Shroff, Mumbai (IN); Paresh Vithaldas Talati, Mumbai (IN)

(73) Assignee: UPL LIMITED, Mumbai (IN)

( * ) Notice: Subject to any disclaimer, the term of this patent is extended or adjusted under 35 U.S.C. 154(b) by 6 days.

(21) Appl. No.: 14/896,812

(22) PCT Filed: Jun. 10, 2014

(86) PCT No.: PCT/IB2014/062093
§ 371 (c)(1),
(2) Date: Dec. 8, 2015

(87) PCT Pub. No.: WO2014/199293
PCT Pub. Date: Dec. 18, 2014

(65) Prior Publication Data
US 2016/0120177 A1      May 5, 2016

(30) Foreign Application Priority Data
Jun. 12, 2013   (IN) .............................. 704/KOL/2013

(51) Int. Cl.
*A01N 25/30* (2006.01)
*A01N 57/20* (2006.01)

(52) U.S. Cl.
CPC ............. *A01N 25/30* (2013.01); *A01N 57/20* (2013.01)

(58) Field of Classification Search
None
See application file for complete search history.

(56) References Cited

U.S. PATENT DOCUMENTS

| 3,527,593 | A | 9/1970 | Bland |
| 5,491,125 | A * | 2/1996 | Albrecht ................ A01N 25/30 504/206 |
| 6,284,286 | B1 | 9/2001 | Arimoto |
| 6,451,731 | B1 * | 9/2002 | Agbaje .................. A01N 25/04 504/118 |
| 6,887,830 | B2 | 5/2005 | Stridde |
| 2012/0172229 | A1 | 7/2012 | Nguyen |
| 2013/0195946 | A1 * | 8/2013 | Stamper ............... A01N 25/006 424/405 |

FOREIGN PATENT DOCUMENTS

WO         2004107862         12/2004

OTHER PUBLICATIONS

Stock, "Possible mechanisms for Surfactant-Induced Foliar Uptake of Agrochemicals", Pestic. Sci. 1993, vol. 38, pp. 165-177.

* cited by examiner

*Primary Examiner* — Alton N Pryor
(74) *Attorney, Agent, or Firm* — Cantor Colburn LLP

(57) ABSTRACT

A liquid herbicide composition is provided comprising at least an electrolytic agrochemical active; at least an alkyl N,N-dimethylamine N-oxide, and at least one ($C_9$-$C_{20}$) alkyl sulfosuccinic acid mono ester salt.

10 Claims, No Drawings

AGROCHEMICAL FORMULATIONS

FIELD OF THE INVENTION

The present invention relates to liquid herbicide compositions.

BACKGROUND

Liquid herbicidal compositions are well known. They are either prepared from solid compositions by contacting with appropriate solvents or are made available in the ready-to-use liquid form. The activity of such composition and consequently their efficacy in weed control is largely dependent on the bioavailabilty of the actives in the target weeds. Additionally, conventional liquid herbicidal compositions sometimes tend to be unstable leading to settling down of the ingredients. Depending on the nature of the actives various stability enhancing agents are added to such conventional herbicidal compositions. Such agents include surfactants.

It is known from the art that organophosphorous compounds such as glufosinate possess a good and broad activity against weeds of many botanical families. The ammonium salt of these compounds is particularly important. They are usually formulated as aqueous solutions. Both spreadability and adhesion are major criteria for agrochemical formulations which are sprayed onto waxy plant surfaces. The ability to spread quickly and uniformly on the waxy part of plant surfaces enables quick uptake of the agrochemical resulting in greater bioavailability of the active molecule to the plant. In case of aqueous formulations of herbicides such as glufosinate, both spreadability and adhesion improves the effect of the herbicidal activity on the weed.

U.S. Pat. No. 5,491,125 (Albrecht et. al) discloses the use of several class of surfactants which may be used to formulate organophosphorus based herbicides. The patent however, discloses in examples that use of certain surfactants results in a cloudy formulation, which is known to occur due to phase separation within the formulation. The formulations disclosed here are not generally stable.

U.S. Pat. No. 6,887,830 (Stridde et. al.) discloses that the bioefficacy of amine based surfactants can be enhanced by adding sulfosuccinate based surfactants. The volume of surfactants needed is between 25 to 45% of the total composition out of which, 45% to 60% by mass of the surfactant component comprises the amine based surfactant which is a fatty amine alkoxylate. The patent discloses the preparation of such sulfosuccinate esters, with acid and hydroxy-bearing hydrophobes such as alcohol alkoxylates resulting in a mixture of alkoxylated mono and diesters of sulfosuccinate. Due to the presence of such hydrophobes it often leads to haziness in aqueous medium thereby indicating incompatibility of these surfactants with electrolytic agrochemicals in aqueous formulations.

U.S. Pat. No. 3,527,593 (Bland et. al) discusses the amine oxide surfactants and their spreadability when combined with alcohols.

US 2012/0172229A1 (Nguyen et. al) discloses the use of a ($C_3$-$C_8$)monoalkyl sulfosuccinate ester as a compatibilizing agent along with a high load of pesticides and other surfactants.

None of the compositions in the prior art, however, provide a composition that is sufficiently stable, environment friendly as well as shows significant weed control. There is, therefore, a need in the art for a liquid herbicide composition that is stable and demonstrates excellent weed control apart from being environmentally benign.

SUMMARY OF THE INVENTION

The present invention relates to a liquid herbicide composition comprising:
at least an electrolytic agrochemical active;
at least an alkyl N,N-dimethylamine N-oxide, at least an anionic surfactant and optionally at least a fatty amine alkoxylate.

OBJECT OF THE INVENTION

It is an object of the invention to provide liquid herbicide composition of low toxicity, comprising an electrolytic active ingredient.

It is an object of the invention to provide a composition that demonstrates excellent bioactivity.

It is another object of the invention to provide a composition with excellent penetration capability.

It is another object of the invention to provide a composition with excellent adhesion capabilities.

It is another object of the invention to provide a herbicidal composition that demonstrates excellent rainfastness and bioefficacy.

It is yet another object of the present invention, to provide a liquid herbicidal composition that contains lower concentrations of surfactants, thereby making the composition more environmental friendly.

DETAILED DESCRIPTION OF THE INVENTION

Surprisingly it has been found that compositions comprising electrolytic agrochemicals, N-oxide surfactants such as alkyl N, N-dimethylamine N-oxide and anionic surfactants optionally with fatty amine alkoxylates demonstrate enhanced bioefficacy towards weed control in comparison with the conventionally known herbicidal compositions. The composition of the present invention also demonstrate higher physical stability not observed in the prior art. Moreover, the higher efficacy of the composition of the invention is achieved using lower total percentages of the surfactants. There can however be variations in the amount of the individual surfactants added to the composition depending on the type of active ingredient employed, the percentage of the active ingredient and the target crop.

In an embodiment, the invention provides a herbicidal composition comprising alkyl N, N-dimethylamine N-oxide as a surfactant wherein the alkyl group is a $C_8$-$C_{20}$ carbon chain alkyl group. Examples of ($C_8$-$C_{20}$)alkyl dimethylamine N-oxide include decyl-, dodecyl, tetradecyl-, pentadecyl-, and hexadecyl N,N-dimethylamine oxides. The preferred amine N-oxide is tetradecyl dimethylamine oxide which also referred to as Myristyl dimethylamine N-Oxide.

In another embodiment ($C_8$-$C_{20}$)alkyl N, N-dimethylamine N-oxide may be present in an amount from about 0.1 to about 10% by weight, preferably from about 1 to about 9% by weight of the composition.

In an embodiment, the anionic surfactant may be selected from salts of alkyl sulfosuccinic acid diesters or monoesters having an alkyl chain of length C-9 and above, fatty alcohol polyglycol ether sulfate, alkyl sulfate and its salts. In an embodiment, the anionic surfactant may be selected from the salts of ($C_9$-$C_{20}$)alkyl sulfosuccinic acid monoesters.

In another embodiment the anionic surfactant may be present in an amount from about 0.1 to about 20% by weight, preferably in an amount from about 1 to about 15% by weight of the composition.

In yet another embodiment the ratio of alkyl N, N-dimethylamine N-oxide and salts of alkyl sulfosuccinic acid monoesters of the present invention varies from about 1:1 to about 1:10.

In an embodiment, the fatty amine alkoxylate denotes a compound of the formula:

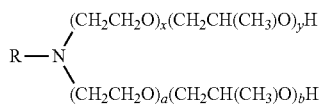

wherein R is a $C_8$-$C_{25}$ alkyl, x and a are moles of ethylene oxide and y and b being moles of propylene oxide.

In an embodiment, x and a may be identical or different and may be selected from 1 to 100.

In another embodiment, y and b may be same or different and may be selected from 1 to 100.

In a preferred embodiment the fatty amine alkoxylate may be selected from ethoxylated amine derivatives of fattyamines such as olelylamine, stearylamine, tallowamine and cocoamine. The most preferred fatty amine alkoxylate being oleylamine ethoxylate.

In another embodiment the fatty amine alkoxylate may be present in an amount from about 0.1 to about 5% by weight, preferably in an amount from about 0.1 to about 3% by weight of the composition.

The compositions of the present invention contain one or more herbicidally active ingredients. In an embodiment an electrolytic agrochemical is selected from various classes of herbicides and mixtures thereof.

The herbicidally active ingredients that can be present in the composition of the invention include water soluble herbicidal salts. Examples of such herbicides are lactofen, fomesafen and its salts, Pyrimidinyloxybenzoic analogue herbicides such as pyrithiobac sodium, bispyribac sodium; Organophosphrous based herbicides such as glyphosate and it salts, glufosinate and its salts, glufosinate-P and its salts, bilanafos and its salts, bialaphos and its salts; Bipyridinium herbicides such as paraquat and diquat and salts thereof; aryloxyalkanoic acid herbicides such as 2,4-D and its salts, MCPA and its salts, MCPB and their salts; Pyridine herbicides such as triclopyr, picloram, aminopyralid and salts thereof; Aromatic herbicides such as dicamba, 2,3,6-TBA, tricamba and their salts; Pyridinecarboxylic acid herbicides such as clopyralid; Imidazolinones selected from imazameth, imazamethabenz, imazamox, imazapic, imazapyr, imazaquin, imazethapyr or mixtures of such herbicides.

Preferred herbicides include glufosinate and its salts.

According to an embodiment of the present invention, the ammonium salt of glufosinate is the preferred salt.

According to another embodiment of the present invention, composition comprises from about 1% to about 50% by weight of glufosinate ammonium salt, preferably from about 5% to about 50% by weight of the composition.

Optionally fungicides, non-electrolyte based herbicides, insecticides, biocides, as well as fertilizers, micronutrients, may also be added to the composition of the invention.

The herbicidal composition of the invention may further comprise other agronomically suitable excipients such as auxiliary adjuvants for example ammonium sulfate, other surfactants, solvents, pH modifiers, crystallization inhibitors, viscosity modifiers, suspending agents, spray droplet modifiers, pigments, antioxidants, light-blocking agents, compatibilizing agents, antifoam agents, sequestering agents, neutralizing agents, corrosion inhibitors, dyes, odorants, spreading agents, penetration aids, emolients, lubricants, sticking agents, dispersing agents, thickening agents, freezing point depressants, antimicrobial agents, and the like.

The anti-foaming agents may be selected but are not limited to silicon based and non-silicone based agents. The silicone based agents may be selected from silicone oil, polydimethylsiloxane and the non-silicone based agents may be selected from mineral oil based antifoams, alcohols like n-octanol, vegetable oils, fatty acids, fatty amines, polyalkylene glycol, tributyl phosphate.

The anti-drift agents may be selected from polyacrylamides, the polyethylene oxides, and the poly (vinyl pyrrolidones), with the polyacrylamide, naturally derived guars and other polysaccharide based anti-drift agents and mixtures thereof.

The solvents may be selected from, but are not limited to alkyl benzene; naphthalene and its derivatives/analogs; alkyl esters of pthalic acid and trimellitic acid; aromatic hydrocarbons such as such aromatic 100, aromatic 200, mixtures of aromatics aliphatic or cycloaliphatic hydrocarbon such as hexane and heptanes; ketones such as cyclohexanone, octanone or acetophenone; chlorinated hydrocarbons; vegetable oils and modified vegetable oils; glycols and their derivatives; aliphatic alcohols or mixtures of such two or more solvents. Other solvents can be alkylene carbonates (like propylene carbonate, ethylene carbonate), morpholine based solvents, fatty alkyl amides (selected from $C_{10}$ amides and $C_8$-$C_{10}$ amides), esters such as alkyl esters of carboxylic acids or mixtures thereof.

The colouring agents maybe selected from various formulation dyes known in the art.

The compositions according to the present invention may be formulated as liquid compositions such as soluble liquids; suspension concentrates, micro-emulsions, emulsions oil-in-water or water-in-oil, suspo-emulsions, etc. The processes for preparing such composition are known in the art and are not particularly limiting.

The compositions according to the present invention can contain single active or a combination of more than one active. The composition can be prepared by tank-mixing with other actives or alternatively may be sold as a kit of parts containing actives and other ingredients that may be mixed prior to spraying or a ready mix kit of parts containing premixed ingredients and actives described above.

The compositions according to the present invention have many distinct advantages. Firstly the composition uses very low amount of surfactants as compared to the composition known in the prior art. The composition allows a high load of active ingredient while having low surfactant content yet demonstrates higher stability, excellent spreadability and adhesion and superior bio-availability leading to better bio-efficacy as compared to compositions known in the art.

These and other advantages of the invention will become more apparent from the examples set forth herein below. These examples are provided merely as illustrations of the invention and are not intended to be construed as a limitation thereof.

EXAMPLES

Example 1: Method of Preparation of Composition

A composition of glufosinate-ammonium and glyphosate isopropyl ammonium was prepared according to the present invention:

| Ingredients | % (w/w) |
|---|---|
| Glufosinate ammonium | 14.90 |
| Glyphosate isopropyl ammonium | 18.20 |
| Prolylene Glycol | 4.00 |
| 1-Methoxy-2-propanol | 1.50 |
| Ammonium sulfate | 0.10 |
| Coco N,N-dimethylamine N-Oxide | 6.00 |
| (C9-C20)alkyl sulfosuccinic acid mono ester sodium salt | 12.00 |
| Anti-foaming agents | 0.50 |
| water | 42.80 |
| Total | 100.00 |

The composition was prepared by in the following manner:

a. Purified glufosinate ammonium and glyphosate isopropyl ammonium were mixed in a formulation vessel with solvents followed by the addition of the two surfactants one after the other. The resultant mixture was homogenized to obtain a clear transparent solution.

b. To the solution obtained in step a, ammonium sulfate and anti-foaming agents were added.

c. The pH of the solution was then adjusted to obtain a pH stable composition which was then filtered to remove solid impurities. The formulation was then diluted with water.

Example 2

The compositions according to the present invention have been demonstrated by the samples given in table 1.

General Process:

The compositions were prepared by in the following manner:

a. The active ingredient was mixed in a formulation vessel with the solvents followed by the addition of the surfactants one after the other. The resultant mixture was homogenized to obtain a transparent solution.

b. The pH of the solution was adjusted to obtain a pH stable composition which was then filtered to remove any solid impurities. The formulation was then diluted with water.

Table I demonstrates various composition samples prepared using different active ingredients and various ratios of the surfactants. The prepared samples were tested for physical stability at various temperatures and for bioefficacy.

TABLE 1

| Composition sample number | Active ingredient | (% by wt.) | Solvents: X:Y (% by wt.) | Amine N-oxide (% by wt.) | Sulfosuccinate$^a$ (% by wt.) | Amine ethoxylate (% by wt.) | Sulfosuccinate$^g$ (% by wt.) |
|---|---|---|---|---|---|---|---|
| 1 | A | 26.11 | 0:29 | 4.0$^b$ | 6.0 | 0.2$^c$ | 0.0 |
| 1a | A | 26.11 | 31:0 | 4.0$^d$ | 8.0 | 0.2$^e$ | 0.0 |
| 2 | A | 14.42 | 16:6 | 4.0$^f$ | 6.0 | 0.0 | 0.0 |
| 3 | A | 26.11 | 16:6 | 3.0$^f$ | 6.5 | 0.2$^c$ | 0.0 |
| 4 | A | 12.21 | 16:6 | 4.0$^f$ | 6.0 | 0.0 | 0.0 |
| 5 | A | 26.11 | 16:2 | 0.0 | 12.0 | 0.0 | 0.0 |
| 5a | A | 26.11 | 16:6 | 0.0 | 6.0 | 0.0 | 0.0 |
| 6 | A | 26.11 | 15:4 | 10.0$^f$ | 0.0 | 0.0 | 0.0 |
| 6a | A | 26.11 | 16:6 | 3.0$^f$ | 0.0 | 0.0 | 0.0 |
| 7 | A | 26.11 | 16:6 | 0.0 | 0.0 | 0.0 | 0.0 |
| 8 | A | 12.21 | 16:6 | 4.0$^f$ | 0.0 | 0.0 | 6.0 |
| 9 | A | 26.11 | 16:6 | 6.0$^f$ | 0.0 | 0.0 | 12.0 |
| 10 | A + B | 14.9:18.2 | 4:1.5 | 6.0$^f$ | 12.0 | 0.0 | 0.0 |

A: glufosinate ammonium,
B: Glyphosate isopropylammonium,
X: propylene glycol,
Y: 1-methoxy-2-propanol,
$^a$(C$_9$-C$_{20}$)alkyl sulfosuccinic acid mono ester sodium salt;
$^b$lauryl N,N-dimethylamine N-oxide;
$^c$oleylamine ethoxylate;
$^d$coco N,N-dimethylamine N-oxide;
$^e$tallowamine ethoxylate;
$^f$myristyl N,N-dimethylamine N-oxide;
$^g$sulfosuccinate trialkyl ammonium salt of U.S. Pat. No. 6,887,830-example1c

TABLE 2

Comparative study of physical stability and weed control of the samples prepared in Table 1

| Composition sample number | Appearance at 25° C. after 14 days | Appearance at 0° C. after 14 days | Appearance at −10° C. after 14 days | % weed control$^a$ |
|---|---|---|---|---|
| 1 | Clear | Clear | Clear | — |
| 1a | Clear | Clear | Clear | — |
| 2 | Clear | Clear | Clear | 98% |
| 3 | Clear | Clear | Clear | 95% |
| 4 | Clear | Clear | Clear | 90% |
| 5 | Clear | Clear | Clear | 56% |
| 5a | Clear | Clear | Clear | — |
| 6 | Clear | Clear | Clear | 60% |

TABLE 2-continued

Comparative study of physical stability and weed
control of the samples prepared in Table 1

| Composition sample number | Appearance at 25° C. after 14 days | Appearance at 0° C. after 14 days | Appearance at −10° C. after 14 days | % weed control[a] |
|---|---|---|---|---|
| 6a | Clear | Clear | Clear | — |
| 7 | Clear | Clear | Clear | 45% |
| 8 | Hazy | Layer separation | Layer separation | — |
| 9 | Hazy | Hazy and Layer separation | sedimentation | — |
| 10 | Clear | Clear | Clear | — |
| 11 | Clear | Clear | Clear | — |

[a] weeds include *Alternenthera sessilis* and *Parthenium hysterophorus*. The weeds were sprayed with the sample compositions of Table 1 at the dilution and rate as per recommended dose and % weed control was found out 7 days after application.

From the above experiments it has been found that samples 1, 1a, 2, 3 and 4 according to the present invention resulted in stable composition. Samples 2, 3 and 4 having varied concentrations of the active ingredient were tested in the field and exhibited good weed control. Although samples 5, 5a which did not have the alkyl N, N-dimethylamine N-oxide and samples 6, and 6a which did not have alkyl sulfosuccinic acid monoester salt resulted into stable compositions, they were found to be unsatisfactory in imparting effective weed control. It was also noted that the bioefficacy was very poor when both alkyl N, N-dimethylamine N-oxide and salts of alkyl sulfosuccinic acid monoesters were absent in the composition as evidenced by sample 7. Samples 8 and 9 using sulfosuccinate based surfactant of U.S. Pat. No. 6,887,830 were found to be unstable indicating the incompatibility of the surfactants with electrolytic agrochemicals and hence weed control was not tested.

Field Trials:

Protocol:

Field trials were carried out using the compositions of glufosinate ammonium prepared according to the present invention as the broad spectrum herbicide. The composition were diluted with water and optionally mixed with other tank mix auxiliaries and applied at a water application rate of 300-500l/ha to crop and non-crop land containing many broad leaf weeds, grasses and sedges. Observations 14 days after treatment have been summarized in below tables demonstrating the bio-efficacy of the compositions.

Weed Control Study in Corn Field

Samples 2, 3 and 4 according to the present invention as well as a comparative sample prepared according to the prior art were tested for weed control in corn fields.

TABLE 3

Weed control study in corn fields
Field experiment on Giant Ragweed and Purslane in corn field
Action in per cent weed control 14 days after treatment
Water application rate: 300 litres/ha

| Composition sample | Giant Ragweed Dosage: g of active substance/ha | | Purslane Dosage: g of active substance/ha | |
|---|---|---|---|---|
| | 227 gha$^{-1}$ | 454 g/ha$^{-1}$ | 227 gha$^{-1}$ | 454 g/ha$^{-1}$ |
| Comparative sample* | 75.0 | 82.5 | 75.0 | 82.5 |
| Sample 2 | 82.0 | 98.0 | 85.0 | 99.0 |
| Sample 3 | 77.5 | 95.0 | 77.0 | 87.5 |
| Sample 4 | 79.0 | 90.0 | 80.0 | 90.0 |

*sample prepared according to example 11 of US 2005/0266999A1

Since samples 8 and 9 using sulfosuccinate based surfactant of U.S. Pat. No. 6,887,830 were not suitable for testing the bioefficacy (due to unstability of the samples), the weed control of compositions according to the present invention were compared with sample prepared as per example 11 of US 2005/0266999. Good weed control was observed for samples prepared according to the present invention.

Weed Control Study in Sweet Almond Field

Samples 2, 3 and 4 according to the present invention as well as a comparative sample prepared according to the prior art were tested for weed control in sweet almond field.

TABLE 4

Weed control study in sweet almond field
Field experiment on Whitestem filaree and
*Hordeum* sp. Barley in Sweet almond field
Action in per cent weed control 14 days after treatment
Water application rate: 300 litres/ha

| Composition sample | Whitestem filaree Dosage: g of active substance/ha 454 g/ha$^{-1}$ | *Hordeum* sp. Barley Dosage: g of active substance/ha 454 g/ha$^{-1}$ |
|---|---|---|
| Comparative sample* | 89.0 | 80.0 |
| Sample 2 | 100.0 | 98.0 |
| Sample 3 | 96.0 | 96.0 |
| Sample 4 | 94.0 | 94.0 |

*sample prepared according to example 11 of US 2005/0266999A1

Excellent weed control was observed for samples prepared according to the present invention.

Table 5: Weed Control Study in Broad Leaf Weeds

Samples 2, 3 and 4 prepared according to the present invention were tested in broad leaf weeds for weed control efficacy. Also sample 5 (which do not contain alkyl N, N-dimethylamine N-oxide), sample 6 (which do not contain salt of alkyl sulfosuccinic acid monoester) and sample 7 (which do not contain both alkyl N, N-dimethylamine N-oxide and salt of alkyl sulfosuccinic acid monoester) were tested for weed control.

TABLE 5

Weed control study in broad leaf weeds

| Composition sample | % Weed control | |
|---|---|---|
| | *Alternenthera sessilis* 14 DAS | *Parthenium hysterophorus* 14 DAS |
| Sample 4 | 78.35 | 78.35 |
| Sample 3 | 79.63 | 80.90 |
| Sample 5 | 68.67 | 56.25 |
| Sample 2 | 76.56 | 70.13 |
| Sample 6 | 68.90 | 60.0 |

TABLE 5-continued

Weed control study in broad leaf weeds

| Composition sample | % Weed control | |
|---|---|---|
| | *Alternenthera sessilis* 14 DAS | *Parthenium hysterophorus* 14 DAS |
| Sample 7 | 48.00 | 45.00 |
| control | 00.00 | 00.00 |

It was thus found that the samples for various strengths of glufosinate according to the present invention exhibited good weed control while the samples without alkyl N,N-dimethylamine N-oxide and/or alkyl sulfosuccinate mono ester sodium salt did not exhibit the effective weed control.

The instant invention is more specifically explained by above examples. However, it should be understood that the scope of the present invention is not limited by the examples in any manner. It will be appreciated by any person skilled in this art that the present invention includes aforesaid examples and further can be modified and altered within the technical scope of the present invention.

The invention claimed is:

1. An aqueous liquid herbicide composition comprising at least one herbicide comprising glufosinate, at least one solvent, at least one ($C_8$-$C_{20}$)alkyl N,N-dimethylamine N-oxide, and about 1 to about 15% by weight of an ($C_9$-$C_{20}$)alkyl sulfosuccinic acid mono ester salt, wherein a ratio of said ($C_8$-$C_{20}$)alkyl N,N-dimethylamine N-oxide and ($C_9$-$C_{20}$)alkyl sulfosuccinic acid mono ester salt varies from about 1:1 to about 1:10, wherein the liquid herbicide composition remains clear at 0° C. or −10° C. after 14 days, and wherein the composition comprising both the alkyl N,N-dimethylamine N-oxide and the alkyl sulfosuccinic acid mono ester salt demonstrates better weed control over the same composition lacking either the alkyl N,N-dimethylamine N-oxide or the alkyl sulfosuccinic acid mono ester salt.

2. The herbicide composition of claim 1 further comprising a ($C_8$-$C_{25}$) alkylamine alkoxylate.

3. The herbicide composition of claim 1 wherein said ($C_8$-$C_{20}$)alkyl N,N-dimethylamine N-oxide is selected from the group consisting of decyl-, dodecyl, tetradecyl-, pentadecyl- and hexadecyl-N,N-dimethylamine oxides.

4. The herbicide composition of claim 2 wherein said ($C_8$-$C_{25}$) alkylamine alkoxylate is selected from the group consisting of olelylamine, stearylamine, tallowamine, and cocoamine ethoxylates.

5. The herbicide composition of claim 1 wherein said herbicide is a water soluble herbicidal salt.

6. The herbicide composition of claim 1 wherein said herbicide is glufosinate ammonium.

7. The herbicide composition of claim 6 wherein said glufosinate ammonium is present in an amount from about 1 to about 50% by weight of the composition.

8. The herbicide composition of claim 1 wherein said ($C_8$-$C_{20}$)alkyl N,N-dimethylamine N-oxide is present in amount from about 0.1 to about 10% by weight of the composition.

9. The herbicide composition of claim 1 wherein said ($C_9$-$C_{20}$)alkyl sulfosuccinic acid mono ester salt is present in an amount from about 0.1 to about 20% by weight of the composition.

10. The herbicide composition of claim 2 wherein said ($C_8$-$C_{25}$) alkylamine alkoxylate is present in an amount from about 0.1 to about 5% by weight of the composition.

\* \* \* \* \*